US012629023B2

(12) United States Patent
Overjordet et al.

(10) Patent No.: US 12,629,023 B2
(45) Date of Patent: May 19, 2026

(54) SYSTEM FOR FUNDUS IMAGING

(71) Applicant: Oivi AS, Oslo (NO)

(72) Inventors: Hans Einar Overjordet, Oslo (NO); Anders Eikenes, Oslo (NO); Jukka Alasirnioe, Oslo (NO)

(73) Assignee: Oivi AS, Oslo (NO)

( * ) Notice: Subject to any disclaimer, the term of this patent is extended or adjusted under 35 U.S.C. 154(b) by 286 days.

(21) Appl. No.: 18/568,866

(22) PCT Filed: Jun. 14, 2022

(86) PCT No.: PCT/GB2022/051488
§ 371 (c)(1),
(2) Date: Dec. 11, 2023

(87) PCT Pub. No.: WO2022/263803
PCT Pub. Date: Dec. 22, 2022

(65) Prior Publication Data
US 2024/0138672 A1      May 2, 2024

(30) Foreign Application Priority Data

Jun. 15, 2021      (GB) ..................................... 2108512

(51) Int. Cl.
*A61B 3/14*          (2006.01)
*A61B 3/12*          (2006.01)
(52) U.S. Cl.
CPC .............. *A61B 3/1208* (2013.01); *A61B 3/14* (2013.01); *A61B 2560/0431* (2013.01)
(58) Field of Classification Search
CPC ........... A61B 3/1208; A61B 3/14; A61B 3/12; A61B 2560/0431

USPC ......................................................... 351/206
See application file for complete search history.

(56) References Cited

U.S. PATENT DOCUMENTS

| | | | | |
|---|---|---|---|---|
| 2007/0030449 A1* | 2/2007 | Liang | ........................ | A61B 3/14 351/206 |
| 2014/0192324 A1* | 7/2014 | Straub | ................ | G01N 21/4795 351/206 |
| 2015/0131050 A1* | 5/2015 | Bublitz | .................... | A61B 3/12 351/246 |
| 2017/0049323 A1* | 2/2017 | Bublitz | .................... | A61B 3/14 |
| 2017/0181625 A1* | 6/2017 | Kawakami | ............... | A61B 3/14 |
| 2017/0231488 A1* | 8/2017 | Tumlinson | ........... | A61B 3/0041 351/221 |
| 2017/0290507 A1* | 10/2017 | Nozato | ................. | A61B 3/1015 |
| 2019/0269323 A1* | 9/2019 | Cornsweet | ........... | A61B 3/0091 |

FOREIGN PATENT DOCUMENTS

EP          3235421 A1 * 10/2017  ............... A61B 3/10

* cited by examiner

*Primary Examiner* — William R Alexander
(74) *Attorney, Agent, or Firm* — Kevin J Fournier Intellectual Property Legal Services Ltd.; Kevin J Fournier

(57) ABSTRACT

The invention provides an imaging system (102) for imaging a fundus (104) of an eye (106), which has an optical axis (116). The imaging system (102) has a light source (108), an illumination path (118) along which light travels from the light source (108) to the eye (106), a light sensor (10) and imaging optics (44) defining an imaging axis (114), and at least one objective lens (112) aligned with the optical axis (116). At least a part of the illumination path (118) is substantially coaxial with the imaging axis (114), and the optical axis (116) is tilted with respect to the imaging axis (114).

18 Claims, 7 Drawing Sheets

Illumination path     — — — — —
Imaging path           ⋯⋯⋯⋯⋯⋯⋯

Illumination path  – – –
Imaging path  ........

Illumination path – – –
Imaging path ········

SYSTEM FOR FUNDUS IMAGING

The present invention relates to a system for obtaining high quality images of the fundus of an eye.

The fundus of the eye is the interior lining of the eyeball, including the retina, optic disc and macula. A camera used for fundus imaging typically comprises a light source, sensor and objective lens, amongst other, additional optical elements. For fundus imaging, the light is typically delivered to the fundus via one of the same optical elements as are used for the image capture. The optical element may be a lens element, often called the objective lens.

However, incident light is reflected at the surface of the objective lens, cornea, front and back of the eye's lens; this reflected light is often described as "ghost reflections". These obscuring "ghost" reflections are then often captured by the sensor, reducing the quality of the captured fundus image. This is typically corrected for by masking the light source such that only the portion of the objective lens which will image or illuminate the fundus of the eye is used whilst portions of the lens which produce the obscuring reflections are not used. However, it is difficult to eliminate reflections using a masked light source, and a good quality image which may be subsequently used by medical professionals for diagnosis and monitoring of eye conditions is therefore difficult to obtain using this set-up. Therefore, to avoid these obscuring reflections, complex arrangements of mirrors, polarisers and optical element coatings may also be required. However, these arrangements increase the complexity of the imaging system, which increases costs of manufacturing and repair. Further to this, a more complex imaging system tends to be less portable and to require a specialist setting where it can be installed, operated and maintained. For many people however, access to these services is very difficult if they live in remote areas.

According to a first aspect of the present invention there is provided an imaging system for imaging a fundus of an eye, the eye having an optical axis, the system comprising:
- a light source,
- an illumination path along which light travels from the light source to the eye,
- a light sensor and imaging optics defining an imaging axis,
- at least one objective lens aligned with the optical axis; wherein at least a part of the illumination path is substantially coaxial with the imaging axis, and the optical axis is tilted with respect to the imaging axis.

Thus, it will be seen by those skilled in the art that in accordance with the invention, reflections of light from the objective lens surface are not reflected back along the imaging axis but are rather deflected off axis by the tilt angle between the illumination path and the optical axis (and thus the axis of the objective lens). Undesirable obscuring "ghost" reflections are therefore not captured by the sensor. The objective lens may be used for both illumination and imaging and therefore any reflection from the lens surface from the illumination is not reflected back to the sensor. Prior art systems typically use complicated optical elements such as a holed coupling mirror and a black dot mask to prevent obscuring reflections. This means that, at least in embodiments of the invention, the optical design may be simplified as such elements are not necessary to prevent the obscuring reflections. Simplifying the optical design may reduce the mechanical complexity, size and weight of an imaging device which comprises the imaging system in accordance with the invention, increasing the portability and reducing the cost of such an imaging device. In some embodiments, the objective lens has an objective optical axis parallel with, but not necessarily coinciding with, the imaging axis.

In a set of embodiments, the light source is not on the same axis as the sensor and imaging optics which defines the imaging axis. This may simplify the design of the light source which is used to illuminate the eye. In a set of embodiments where the light source is on the same imaging axis as the sensor and imaging optics, a ring light source is used. This would typically be necessary to enable the sensor to image the eye using the reflected light from the fundus without the light source impeding this reflected light from reaching the sensor where the image is captured. In a set of such embodiments, the imaging system further comprises a beam splitter. The beam splitter may be, for example, a half-silvered mirror, regular glass, or a mirror with other optical coatings. The beam splitter may be used to redirect light emitted from the light source such that the part of the illumination path which the light travels along after passing through the beam splitter is substantially coaxial with the imaging axis. In another set of embodiments the light source is a set of individual point sources such as light emitting diode (LED) chips arranged in a ring shape.

In a set of embodiments, the objective lens is tilted and decentred from the imaging axis. The optical axis of the eye is therefore not aligned with the centre of the objective lens in such embodiments. The majority of the incident light to the eye, and reflected light from the eye therefore passes through either the top or bottom half of the objective lens. As a consequence of the tilted optical axis of the eye, decentring of the lens may allow the light passing along the illumination path to the eye and the back-reflected light from the fundus to pass along the imaging axis to the sensor.

In a set of embodiments, one or more motors are provided for moving at least some of the imaging optics along the imaging axis. In a set of embodiments the imaging optics includes one or more additional imaging lenses. This may compensate for the variations in the refractive power of the lenses of human eyes, as well as the variations in the size and shape of eyes which may otherwise result in an image on the sensor which is not focused.

In a set of embodiments, the imaging system further comprises additional optical elements, such as lens elements, an aperture stop, filter, field stop and aperture. The lens elements, aperture stop, filter and field stop may be aligned with the light source. The field stop may control and limit the amount of light which passes through further optical elements in the imaging system. There needs to be a high enough light intensity such that there is a high signal to noise ratio on the captured image on the sensor. The filter may be used to filter out any wavelengths of the incident light which are not desired to be used for the imaging. The field stop may be used to limit the size/angular breadth of the object (the fundus of the eye) which is being imaged by the imaging system. The field stop may be set such that a certain field of view of the fundus of the eye is imaged by the imaging system. The aperture may be aligned with a transparent area within the eye's pupil so that only light reflected from the fundus and passing through this particular aperture will reach the sensor.

In a set of embodiments, the imaging system further comprises one or more wedged optical elements. As the optical axis is tilted away from the imaging axis and the one or more objective lenses are decentred with respect to the optical axis, the image incident on the sensor will be distorted and partially blurred. For example, if an objective lens is decentred such that light only passes through the top half, then the light will have travelled a longer distance inside the lens material on the lower part of the image compared to the top. Wedged optical elements between the objective lens and sensor will therefore compensate for this effect, such that the image detected on the sensor is sharply focused and less distorted.

In a set of embodiments, the light source is arranged to emit light at a first wavelength for focusing, and at a second wavelength for imaging. In a set of embodiments, light at the first wavelength is infra-red (IR) light and light at the second wavelength is visible light. The visible light may be white light, or red, green and blue used to produce RGB images, or it may be a single wavelength or other combination of wavelengths. Visible light causes the pupil of the eye to contract, whereas infrared light does not as it is not visible to the human eye. Therefore, infrared light may be used by the imaging system to adjust the position of the one or more imaging lenses for focus. When focus has been achieved, then visible light may be used to capture an image. Visible light will therefore only be used to illuminate the eye for a short period during which there will be minimal pupil contraction. It is also possible to capture a multispectral image of the fundus, i.e. several narrow wavelength pictures, for example several differing infrared and visible wavelength pictures to create better contrast between the features of the fundus associated with certain medical conditions, blood vessels and background fundus tissue compared to previously described methods for visible imaging.

In a set of embodiments, the one or more objective and additional imaging lenses are achromatic. In a normal imaging system, light emitted at different wavelengths will behave differently while interacting with different optical elements. One such effect is chromatic aberration. As such, if one wavelength is used to focus the light by moving the imaging lenses, then when a second wavelength is used for imaging, the light may no longer be in focus at that wavelength due to the different focal lengths at different wavelengths. An achromatic optical system limits the effect of chromatic aberrations such that light will be focussed similarly at two different wavelengths by the achromatically adjusted optical system. The most common type of achromatic lens is the achromatic doublet, which is composed of two individual lenses made from glasses with different amounts of dispersion. Typically, one element is a negative (concave) element with relatively high dispersion, and the other is a positive (convex) element with lower dispersion. The lens elements are mounted next to each other, often cemented together, and shaped so that the chromatic aberration of one is counterbalanced by that of the other.

In order to remove or reduce unwanted reflections from the lens surface to the image capture sensor, the optical axis is tilted away from the imaging axis at an angle e.g. between 5 and 80°, e.g. between 10 and 60°, e.g. between 20 and 40°. The angle used may vary depending on factors such as the material from which the lens is fabricated, or the wavelength of light used for imaging. If the angle is too large, it may be more difficult to compensate for the distorted and degraded image, resulting in a lower image quality. Additional optical elements may then be required to compensate for the distorted and degraded image caused by the tilted objective lens. On the other hand if the angle is too small, then reflected stray light may still be problematic or the small tolerances required for removal of the obscuring reflections may be difficult to achieve. The angle of tilt may therefore be optimised according to the acceptable complexity (such as additional optical elements) of the imaging system. This optimised angle may be chosen to be just high enough that the light which is reflected from the tilted lens surface, which will be least reflected away from the imaging path, is not captured by the sensor.

In a set of embodiments, the imaging system further comprises a decentred reimaging lens. The decentred reimaging lens may be on the imaging axis, next to the sensor, such that light which has been reflected from the fundus of the eye will have passed through the titled objective lens prior to passing through the decentred reimaging lens. The decentred reimaging lens will be understood to be decentred such that the imaging axis is not aligned with a centre of the reimaging lens. The majority of the reflected light therefore passes through either the top or bottom half of the reimaging lens. The decentred reimaging lens may allow the light from the eye, to be focused onto the sensor. The decentred reimaging lens may act to compensate for the degraded and distorted image caused by the decentred and tilted objective lens such that the image incident on the sensor is improved. Having an image which is improved and not distorted may reduce the amount of image processing necessary and may give clearer final images which enable medical professionals to make diagnoses and monitor conditions more effectively.

In a set of embodiments, the imaging system is incorporated into a fundus imaging device. The device may be portable or fixed.

In a set of embodiments, the imaging device comprises a processor which automatically controls the movement of the imaging lens(es) using a feedback control system. The image of the fundus may be used by the feedback control system for focusing. The focusing may also be manual and using the motors to ensure focus may be carried out by the person performing imaging using the imaging system. Infrared light may be used to illuminate the fundus for the purpose of adjusting the imaging lenses, so that the eye's pupil does not contract. The focusing may be achieved using a contrast method wherein if the movement of the lens increases the contrast then the focus has been improved. "Hill climbing" or "gradient ascent" contrast maximisation may be used for this purpose. The input images may be enhanced prior to any contrast calculations in order to reduce the image noise in the contrast algorithms. The phase detection method may also be used for focusing, by utilising phase detection pixels in the sensor. Additionally, patterns of light may be actively projected onto the fundus, to compensate for partially poor contrast in the fundus at IR wavelengths. In a set of embodiments, the imaging device further comprises a focusing mechanism comprising one or more moveable imaging lenses.

In a further set of embodiments, the focusing mechanism comprises the sensor being moveable relative to the other optical elements.

In a set of embodiments, the processor uses software to correct the distorted and degraded image. The software may correct the image during post-processing, i.e. after the image has been taken to compensate for the degraded image caused by the decentred and tilted objective lens(es) such that the image incident on the sensor is improved. Such implementation of this may require storage of lens distortion values as a calibration data on a memory of the imaging device. After the image is read by the sensor and sent to the processor and memory, calibration data may be read from the memory and correction values may be used to cancel the optical distortion and possibly correct other image artefacts.

By removing or reducing the distortion from the tilted optical axis, the image obtained by the sensor may be analysed more easily. In a set of embodiments, the imaging device further comprises a removable data storage device, such as a flash memory card. This may allow a user to transfer the stored data (such as images of the fundus of the eye) from the imaging device to a storage device reader (e.g., insertion into a memory card slot). The stored images may therefore be analysed by an external medical professional.

In a set of embodiments, the imaging device can communicate with an external system over a wireless link (e.g., over a Radio Frequency (RF) connection such as a connection conforming to the Bluetooth™, Wi-Fi, GSM, 4G/5G standards). The imaging device may be arranged to transmit stored image data from the internal or removable data storage device. An external system may thus receive images of the fundus of the patient's eye which can be reviewed by specialists at another location. The images which have been captured by the imaging device may therefore be used to refer the patient to specialist treatment or further follow-ups.

In a set of embodiments, the imaging device comprises a processor arrangement programmed to perform an artificial intelligence algorithm that analyses captured images and provides information regarding whether a further referral is necessary. In a set of embodiments, the imaging device further comprises a screen. Referral information could be displayed on the imaging device. The same information may also or instead be provided to an external system via the wireless link. The processor arrangement could include the processor previously described or the imaging device could comprise a separate AI processor.

Features of any aspect or embodiment described herein may, wherever appropriate, be applied to any other aspect or embodiment described herein. Where reference is made to different embodiments, it should be understood that these are not necessarily distinct but may overlap.

A non-limiting example will now be described, by way of example only, and with reference to the accompanying figures in which.

Figure 1:
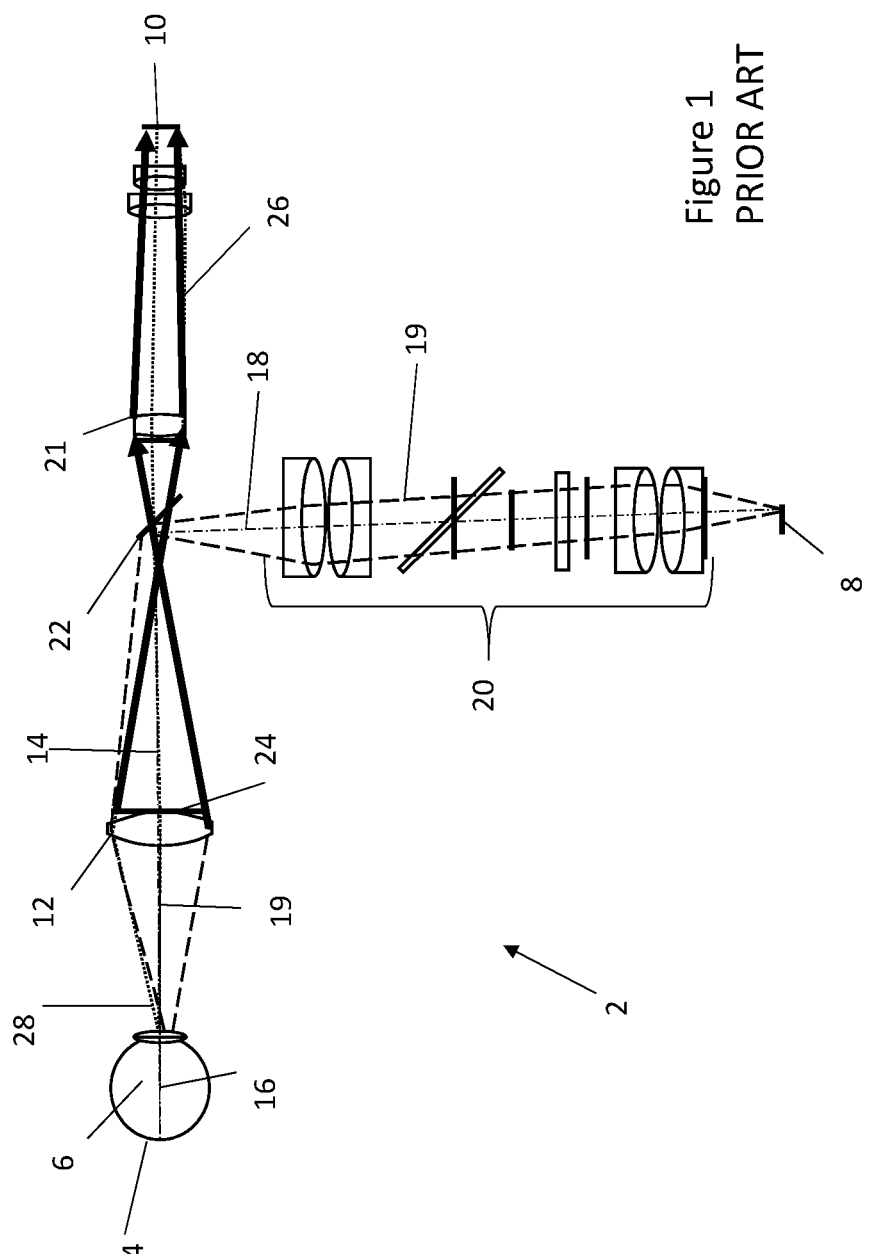
FIG. 1 is a schematic diagram of a prior art imaging system.

FIG. 1 is a schematic diagram of a prior art imaging system 2 used to image the fundus 4 of a patient's eye 6. The imaging system 2 comprises a light source 8, a light sensor 10 forming part of a camera and an objective lens 12. An imaging axis 14 is defined by a line normal to, and extending from the centre of, the light sensor 10, and coinciding with the axis of the further optical elements 21. The optical axis 16 is defined by a line extending from the centre of the macula through the centre of the pupil of the patient's eye 6 to be imaged. In this prior art imaging system 2, both the imaging axis 14 and optical axis 16 are aligned with one another. A beam of light travels from the light source 8 to the eye 6, the centre of the beam defining an illumination path 18 being shown and the edges of the beam being shown by dashed lines 19. Optical elements 20 are distributed along the illumination path 18 between the light source 8 and the eye 6 such that the incident light passes through the optical elements 20 before being reflected from the fundus 4 of the patient's eye 6. Examples of optical elements which may be used in such an imaging system 2 are an aperture stop, filter and field stop.

In order to produce an image of the fundus 4, the light source 8 emits a pulse of light which passes through the optical elements 20. The light is then reflected by a beam splitter 22 such that the downstream portion of the illumination path 18 along which the light is directed is substantially coaxial with the imaging axis 14. The beam splitter 22 directs the incident light along the optical axis 16. The incident light then passes through and is focused by the objective lens 12 onto the fundus 4 of the eye 6. The light is then reflected from the fundus along the imaging axis 14. This reflected light 28 passes back through the objective lens 12, the beam splitter 22, and further optical elements 21 which focus the reflected light 28 onto the sensor 10. The sensor 10 therefore captures an image of the fundus 4 of the eye 6, which may be further stored and analysed if the imaging system 2 is utilised in an imaging device with transmitter and storage capabilities.

As the objective lens 12 is aligned with the optical axis 16, the imaging axis 14, and part of the illumination path 18, incident light on the objective lens 12 is reflected back from the lens surface 24 along the imaging axis 14 and through the optical elements 21 and 22 to the light sensor 10. Both the lens reflections 26 and reflected light from the fundus 28 are captured by the light sensor 10. This reduces the quality of the captured image in prior art systems as the lens reflections 26 may introduce optical artefacts into the captured image, or reduce the signal to noise ratio of the captured image.

Figure 2:
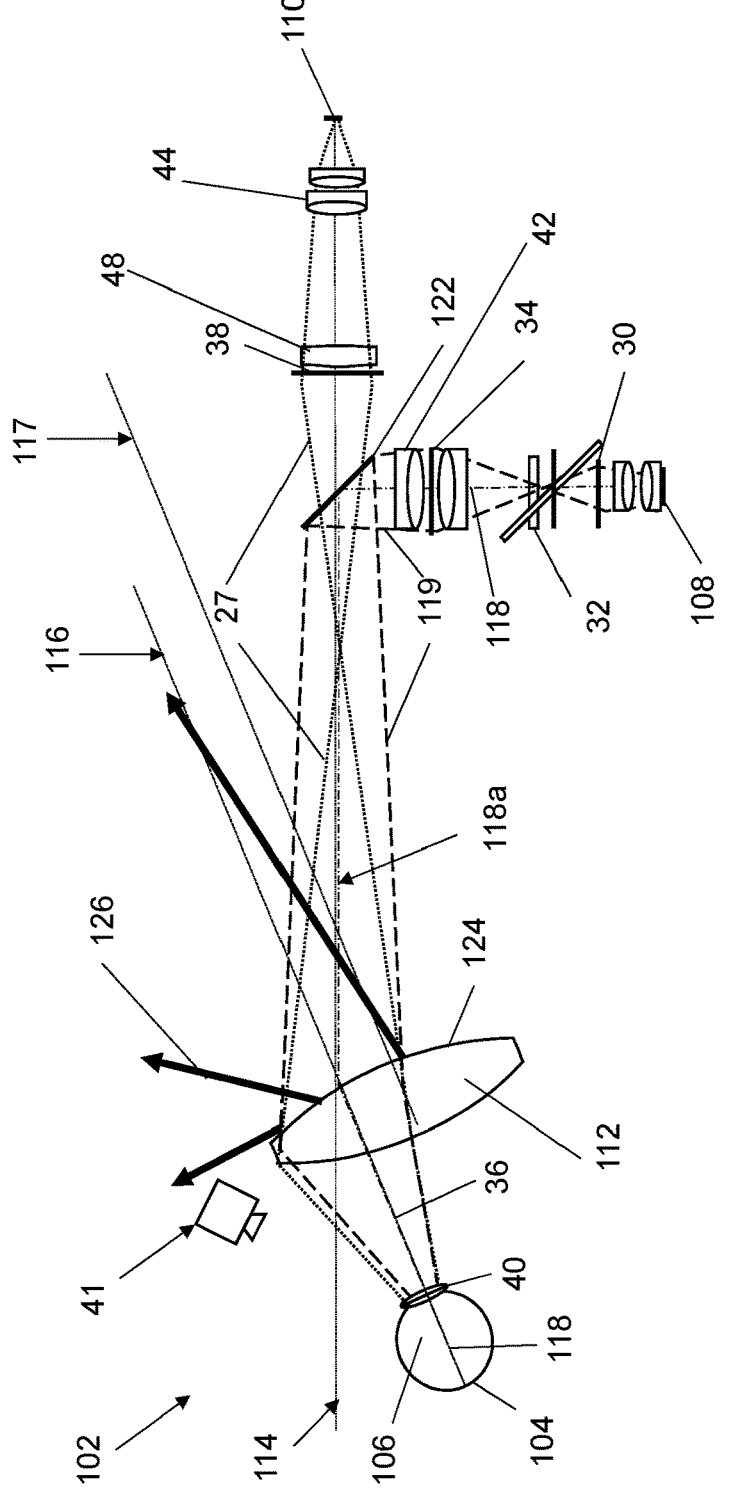
FIG. 2 is a schematic diagram of the imaging system in accordance with the invention used to image the fundus of an eye.

FIG. 2 is a schematic diagram of an imaging system 102 used to image the fundus 104 of a patient's eye 106 in accordance with the present invention. The imaging system 102 comprises a light source 108, sensor 110 and objective lens 112. The imaging axis 114 is aligned with the centre of the sensor 110. The optical axis 116 extends through the centre of the patient's eye 106 to be imaged and is tilted away from the imaging axis 114 in contrast to the prior art imaging system 2 shown in FIG. 1 where the imaging axis 14 and optical axis 16 are aligned. As before, the centre of the beam from the light source 108 defines an illumination path 118. Optical elements including illumination lenses 42, an aperture stop 30, filter 32, field stop 34 and beam splitter 122 are aligned with the illumination path 118 such that incident light from the light source 108 will pass through these elements along the illumination path 118. The edges of the incident beam are shown by the dashed lines 119. The beam splitter 122 may be a half-silvered mirror; other optical coatings may also be used or the beam splitter 122 may be formed from glass.

Figure 3:
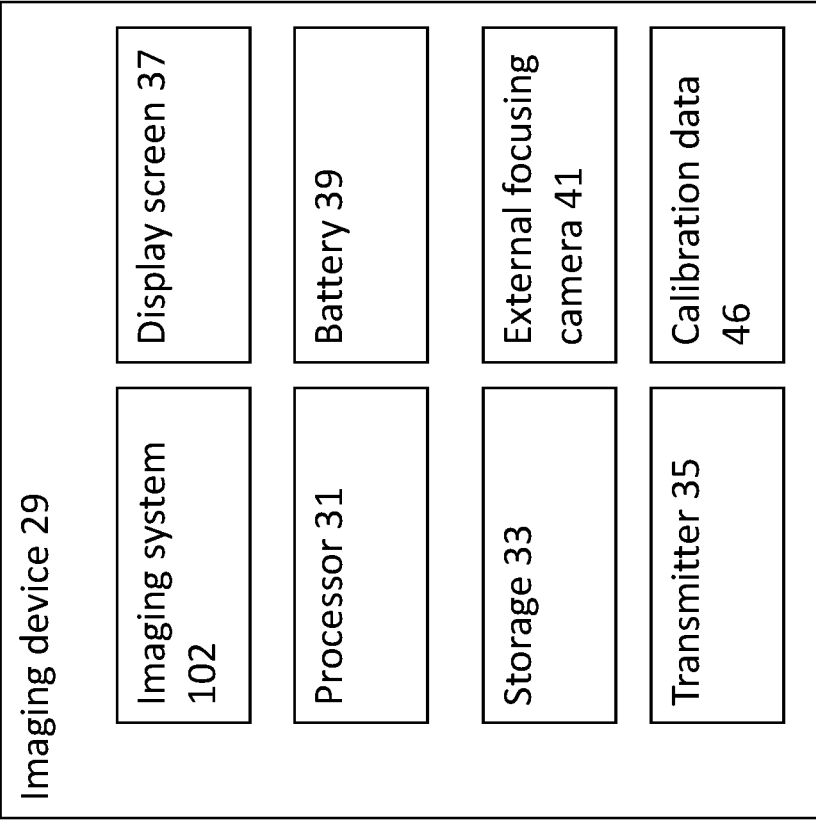
FIG. 3 is a schematic diagram of an imaging device using the imaging system in accordance with the invention.

In order to produce an image of the fundus 104, the light source 108 emits a pulse of light which passes through the aperture stop 30, filter 32, field stop 34, beam splitter 122 and objective lens 112 as shown in FIG. 3, along the illumination path 118. The light is reflected from the fundus 104, and returns through the objective lens 112, beam splitter 122, aperture 38 and imaging optics 44 to produce an image on the sensor 110; the edges of the reflected beam are shown by the dashed lines 27. The aperture stop 30, filter 32 and field stop 34 are aligned with the light source 108 and the illumination path 118. The aperture 38 and imaging optics 44 are aligned with the sensor 110 and the imaging axis 114.

The light emitted by the light source 108 first passes through the aperture stop 30. The aperture stop 30 is an opening which limits the amount of light which passes through the imaging system 102. This is to ensure that enough light is reflected from the fundus 104 such that the sensor 110 can detect the reflected light to form an image, and that not too much light is incident on the fundus 104, thereby preventing overexposure of the sensor 110.

The light may then optionally pass through a filter 32. The filter 32 may be used to filter out any wavelengths of the incident light pulse which are not desired to be used for the imaging and onto the sensor 110 where the reflected light is detected and used to produce an image of the fundus of the patient's eye 104. The focused light then passes through the illumination lenses 42 and the field stop 34.

The light is then reflected off the beam splitter 122 such that the downstream part of the illumination path 118a along which the light passes—is substantially coaxial with the imaging axis 114. The incident light therefore further travels along the illumination path 118a to the objective lens 112.

The light is focused by the objective lens 112 into the patient's eye 106, where it is reflected from the fundus 104. This reflected light 27 follows an imaging path which is substantially coaxial with the illumination path 118 and optical axis of the eye 116. The reflected light 27 is bent by the objective lens 112, such that the path along which the light travels is aligned with the imaging axis 114 (i.e. substantially coaxial). The reflected light 27 passes through the beam splitter 122, aperture 38, and imaging optics 44 where it is focussed onto the sensor 110 to produce an image of the fundus 104 of the patient's eye 106. The axis 117 of the objective lens 112 is parallel with, but does not coincide with the optical axis 116.

As the optical axis 116 is tilted away from the imaging axis 114, incident light on the objective lens 112 is not reflected from the lens surface 124 back along the imaging axis 114, unlike the prior art imaging system 2 shown in FIG. 1. The reflections 126 will therefore not be incident onto the sensor 110, such that unwanted stray light does not fall onto the image sensor. Further to this, the objective lens 112 is decentred with respect to the optical axis of the patient's eye 106 such that incident light on the objective lens 112 can be focused onto the fundus 104 of the eye 106. The light entering the eye 106, and the reflected light from the fundus 104 therefore pass primarily through the top half of the objective lens 112. The decentring of the objective lens 112 is necessary to allow the reflected light from the fundus 104 to be focussed onto the sensor 110 due to the tilt of the lens 112.

As the optical axis 116 is tilted away from the imaging axis 114, reflections of light 126 from the objective lens surface 124 are not reflected back along the imaging axis 114. These undesirable obscuring "ghost" reflections 126 are therefore not captured by the sensor 110, improving the signal to noise ratio compared to an image of the fundus 4 which would be captured by the imaging system 2 shown in FIG. 1.

FIG. 3 is a schematic diagram of an imaging device 29 using the imaging system 102 described with reference to FIG. 2. The imaging device 29 further comprises a processor 31, fixed internal memory or removable data storage medium 33, transmitter 35, display screen 37, battery 39, calibration data 46, and external focusing camera 41 which may in practice be mounted on an exterior portion of the imaging device. The display screen 37 is visible to the user on the imaging device 29, and may contain push-buttons. The processor 31 is programmed to use calibration data 46 for correcting image artefacts such as distortions and colour shading. The processor 31 is also programmed to perform an artificial intelligence algorithm that analyses captured images and provides information on the display screen 37 which outputs the result of this local AI analysis on the captured image. All, or parts of, the AI analysis can be performed by a connected PC or cloud service.

In order to capture an ideal image of the fundus 104, the imaging system 102 must first be focused. The external focusing camera 41 may be used to capture an image of the fundus 104. An automatic focus may be achieved using a feedback control system which comprises the processor 31. The image of the fundus 104 captured by the external focusing camera is input to the processor 31 and an algorithm is then be used to focus the imaging system 102.

In the present example, the light source 108 may be arranged to emit light at two different wavelengths, for example at an infrared and visible wavelength. Initially, light may be emitted at an infrared wavelength. This light will be reflected from the fundus 104 and may be captured by the sensor 110 with the captured images being used to focus the system for the patient's eye 106, by moving the focus lens 48 along the imaging axis 114. Once focus has been achieved, visible light may then be used to illuminate the fundus 104, with the sensor 110 capturing the visible light image which is stored in the data storage medium 33. In this case, the objective lens 112 and the imaging optics 44 may constitute an achromatic optical system such that the focal length at the two different wavelengths is the same.

Alternatively, the external focusing camera 41 detects light at an infra-red wavelength for focusing, and the imaging system 102 may detect light at a visible wavelength for imaging. A common light source could be used for the infra-red and visible light or separate light sources could be used.

The stored images in the data storage medium 33 may then be transmitted by the transmitter 35 to an external server where the images may be viewed and analysed by an algorithm or by a medical professional. Alternatively, the processor 31 may locally analyse the captured images and provide information on the display screen 37 which outputs the result of this local AI analysis on the captured image. The display screen 37 may also be used to display the captured images, such that a medical professional carrying out the imaging could immediately view the images which have been captured by the device 29.

Figure 4:
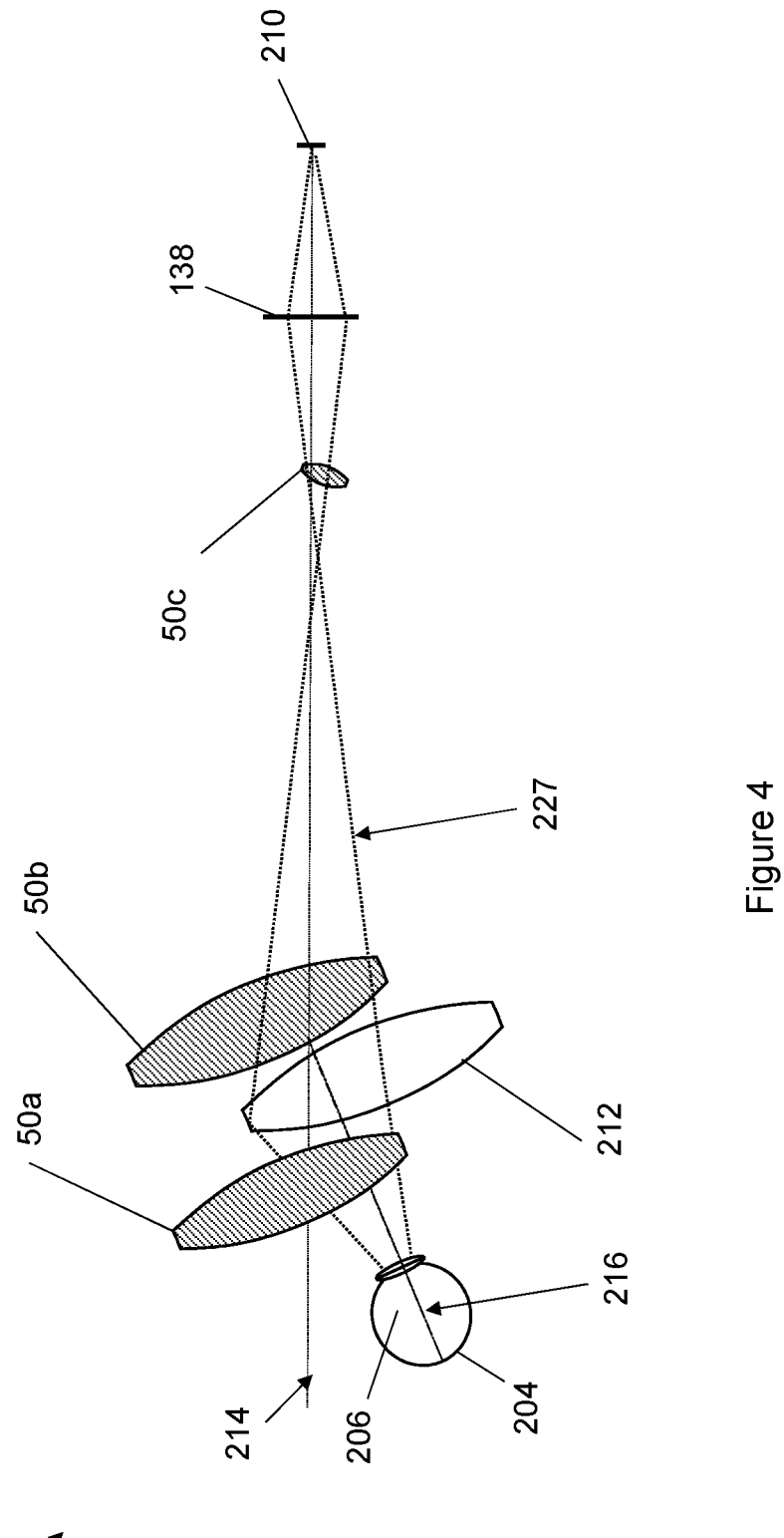
FIG. 4 is a schematic diagram of the imaging system in accordance with the invention including optical correction elements.

FIG. 4 is a simplified schematic diagram of another embodiment of an imaging system 202 in accordance with the invention including optical correction elements 50a-c. Tilting of the lens 212 causes non-symmetrical optical distortions in the image captured by the sensor 210. The distortions can be cancelled partially or fully by introducing wedged optical elements or similarly tilted lenses along the imaging path of the reflected light 227. Three wedged optical elements are shown—50a, 50b, 50c. The elements 50a-c may be also located elsewhere along the imaging path, or there may be more or fewer wedged optical elements. Other parts of the system are the same as described with reference to FIG. 2 but with a prefix '2' instead of '1'.

Figure 5:
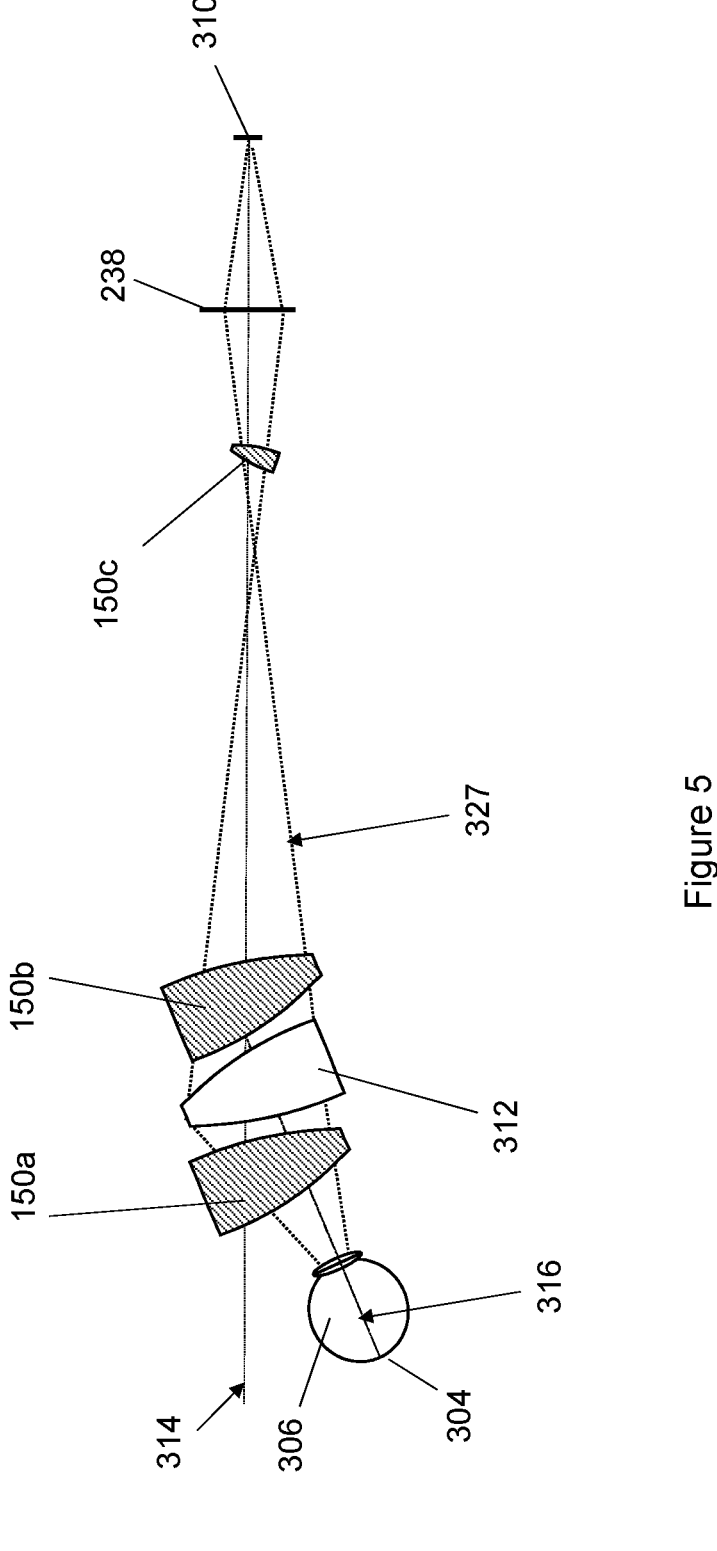
FIG. 5 is a schematic diagram of the imaging system in accordance with the present invention including reduced size optical correction elements.

FIG. 5 is a schematic diagram of a further imaging system 302 in accordance with the invention including reduced size optical correction elements 150a-c. Other parts of the system are the same as described with reference to FIG. 2 but with a prefix '3' instead of '1'. As the total optical area of a decentred lens 312, 150*a*, 150*b* is not used, the unused portion of the lenses may be removed by cutting the lens partially. Alternatively, the lens may be manufactured in the partial wedge shape of lenses 312, 150*a*, 150*b*. Using a lens element with a reduced size reduces the weight of the overall imaging system 302 and helping to further reduce the overall size of the imaging device.

Figure 6:
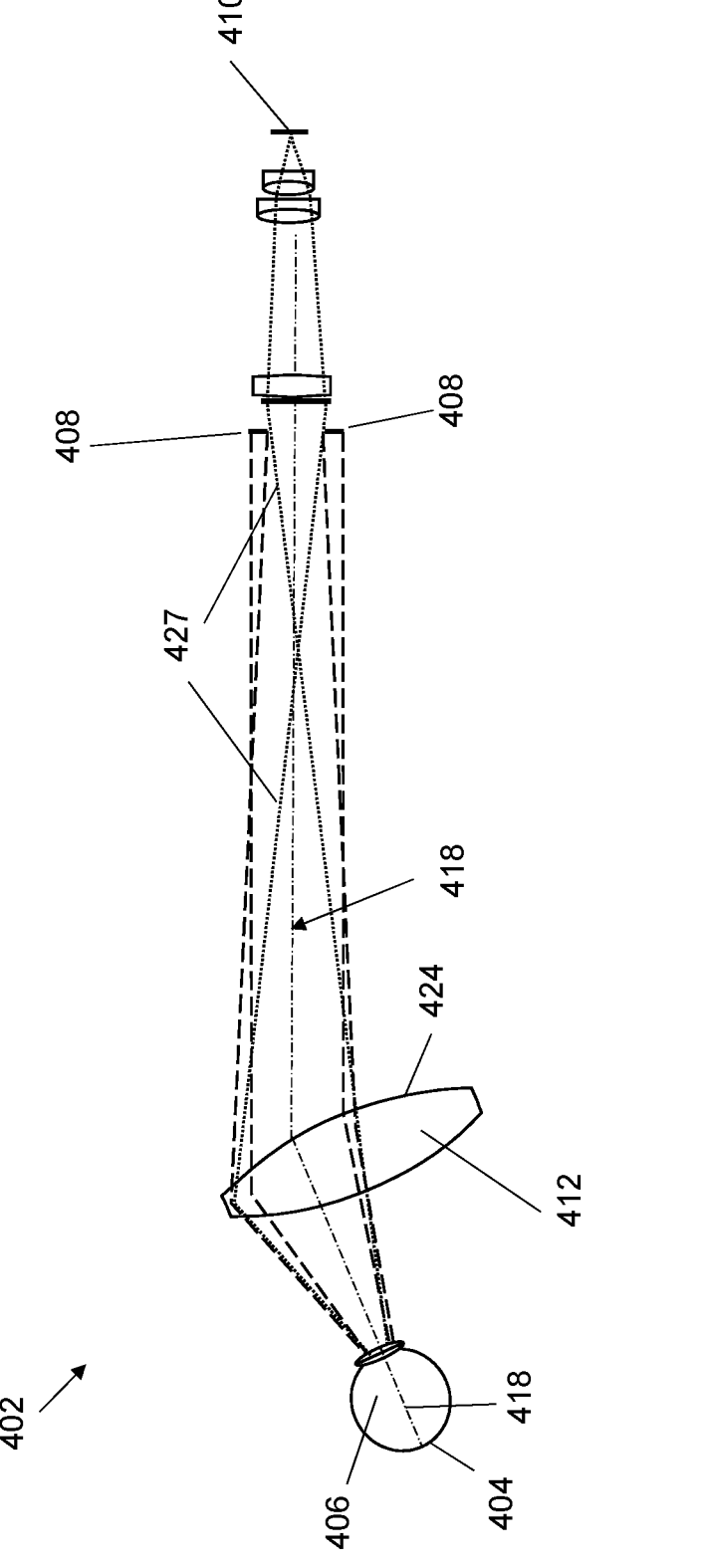
FIG. 6 is a schematic diagram of an imaging system in accordance with the present invention using a ring-shaped light source.

FIG. 6 is a schematic diagram of an imaging system 402 similar to the imaging system 102 of FIG. 2; however the imaging system 402 uses a ring-shaped light source 408 such that the illumination axis 418 and imaging axis 414 are substantially coaxial. The ring light source 408 enables the sensor 410 to image the eye 406 using the reflected light from the fundus 404 without the light source 408 impeding this reflected light from reaching the sensor 410 where the image is captured. Other parts of the system are the same as described with reference to FIG. 2 but with a prefix '4' instead of '1'.

Figure 7B:
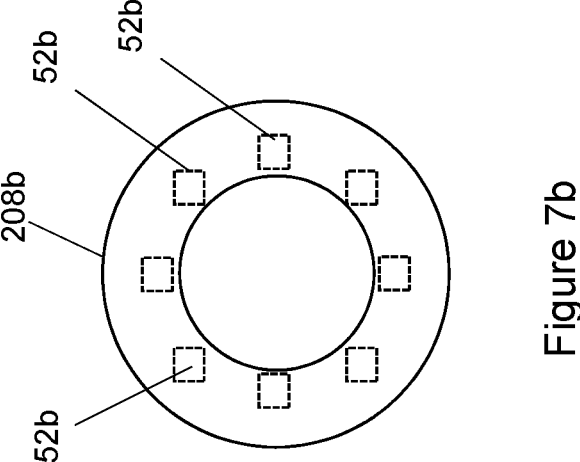
FIG. 7b is a second embodiment of a ring shaped light source using multiple individual sources.
Figure 7A:
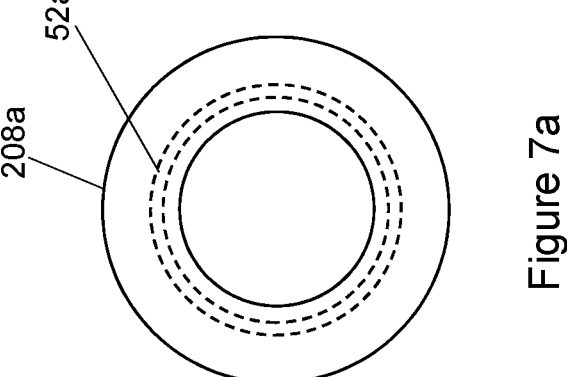
FIG. 7a is an embodiment of a ring shaped light source using a single source.

FIGS. 7*a* and 7*b* show two embodiments of ring-shaped light sources which can be used in the system of FIG. 6 in further detail. FIG. 7*a* shows a light source 408*a* with a circular LED 52*a*. FIG. 7*b* shows a light source 408*b* with multiple individual point sources 52*b*, such as LED chips, arranged in a circular pattern. The quantity of LEDs may vary, with eight LEDs shown in FIG. 7*b*. The wavelengths of each or every LED may be single wavelength, multiple narrow wavelengths, or broadband lights such as white, or any combination of these including lights outside the visible wavelength spectrum, such as infrared (IR) light.

It will be appreciated by those skilled in the art that the invention has been illustrated by describing one or more specific embodiments thereof, but is not limited to these embodiments; many variations and modifications are possible, within the scope of the accompanying claims.

The invention claimed is:

1. An imaging system for imaging a fundus of an eye, the eye having an optical axis, the system comprising:
    a light source, wherein the light source is on the imaging axis,
    an illumination path along which light travels from the light source to the eye,
    a light sensor and imaging optics defining an imaging axis, and
    at least one objective lens aligned with the optical axis;
    wherein at least a part of the illumination path is substantially coaxial with the imaging axis, and the optical axis is tilted with respect to the imaging axis; and wherein the optical axis is tilted away from the imaging axis at an angle of between 5 and 80 degrees.

2. The imaging system of claim 1, wherein the light source is a ring light source.

3. The imaging system of claim 1, further comprising a beam splitter, wherein the beam splitter is used to redirect light emitted from the light source such that the part of the illumination path which the light travels along after passing through the beam splitter is substantially coaxial with the imaging axis.

4. The imaging system of claim 1, wherein the at least one objective lens is tilted and decentered from the imaging axis.

5. The imaging system of claim 1, comprising one or more motors for moving at least some of the imaging optics along the imaging axis.

6. The imaging system of claim 1, wherein the imaging optics comprises one or more additional imaging lenses.

7. The imaging system of claim 1, further comprising a field stop aligned with the light source.

8. The imaging system of claim 1, further comprising one or more wedged optical elements between the objective lens and a light sensor.

9. The imaging system of claim 1, wherein the light source is arranged to emit light at a first wavelength for focusing, and at a second wavelength for imaging.

10. The imaging system of claim 9, wherein the first wavelength is infrared light and the second wavelength is visible light.

11. The imaging system of claim 1, wherein at least one of the objective lens or additional imaging lenses is achromatic.

12. The imaging system of claim 1, further comprising a decentered reimaging lens.

13. The imaging system of claim 12, wherein the decentered reimaging lens is on the imaging axis, such that light which has been reflected from the fundus of the eye will have passed through the titled tilted objective lens prior to passing through the decentered reimaging lens.

14. The imaging system of claim 1, wherein the imaging system is incorporated into a portable fundus imaging device.

15. The imaging system of claim 14, wherein the imaging device comprises a processor arranged to automatically control movement of at least one of the objective lens or additional imaging lenses using a feedback control system.

16. The imaging system of claim 15, wherein the processor is arranged to use software to correct an image of the fundus.

17. The imaging system of claim 14, wherein the imaging device further comprises a focusing mechanism comprising one or more moveable imaging lenses.

18. The imaging system of claim 17, wherein the focusing mechanism comprises a light sensor being moveable relative to the other optical elements.

* * * * *